United States Patent [19]

Guignard et al.

[11] Patent Number: 4,821,708
[45] Date of Patent: Apr. 18, 1989

[54] THERMOFORMABLE ORTHOPEDIC BANDAGE AND USE THEREOF

[76] Inventors: Claude Guignard, Le Vezely/Serby Gare, Saint-Genis-Pouilly, France; Tony Giglio, 15, route des Pilotis, 1246 Corsier-Port; Abdelkader Benmiloud, 55, avenue de Vaudagne, 1217 Meyrin, both of Switzerland

[21] Appl. No.: 21,238

[22] Filed: Mar. 3, 1987

Related U.S. Application Data

[62] Division of Ser. No. 734,314, May 14, 1985, Pat. No. 4,685,453.

[30] Foreign Application Priority Data

May 14, 1984 [CH] Switzerland ............ 2368/84

[51] Int. Cl.⁴ ............................................. A61F 13/00
[52] U.S. Cl. ................................ 128/82.1; 128/68.1; 128/157
[58] Field of Search ............ 128/82.1, 82, 83, 89 R, 128/90, 91 R, 68.1; 428/12, 319.7; 126/204

[56] References Cited

U.S. PATENT DOCUMENTS

| | | | |
|---|---|---|---|
| 1,777,982 | 10/1930 | Popp | 4/535 |
| 2,250,325 | 7/1941 | Barnes | 126/204 |
| 2,802,088 | 8/1957 | MacCracken | 126/204 |
| 2,826,523 | 3/1958 | Blaszkowski et al. | 428/12 |
| 3,326,211 | 3/1964 | Logue et al. | 128/90 |
| 3,662,057 | 5/1972 | Webster et al. | 128/89 R X |
| 3,680,548 | 8/1972 | Brown | 128/69 |
| 3,760,056 | 9/1973 | Rudy | 128/90 X |
| 3,853,124 | 12/1974 | Larson | 128/90 |
| 4,006,741 | 2/1977 | Arluck | 128/90 |
| 4,019,506 | 4/1977 | Eschmann | 128/90 |
| 4,685,453 | 8/1987 | Guignard et al. | 128/90 |

FOREIGN PATENT DOCUMENTS

| | | |
|---|---|---|
| 4829 | 10/1979 | European Pat. Off. . |
| 1215859 | 5/1966 | Fed. Rep. of Germany . |
| 1570760 | 5/1969 | France . |
| 2120515 | 7/1972 | France . |
| 1452795 | 3/1974 | United Kingdom . |

Primary Examiner—Robert A. Hafer
Assistant Examiner—Kevin G. Rooney
Attorney, Agent, or Firm—Cushman, Darby & Cushman

[57] ABSTRACT

The thermoformable element comprises a strip (1) formed from two layers of foam (2, 3) of a thermoplastic polymer. The layers are welded to one another along their longitudinal edges so as to form a space between them in the shape of a channel (4). The inlet for the channel can be controlled by a non-return valve (6) whereas the exit can comprise a plug (7). The element is thermoformed by circulating a fluid heated to 130° to 140° C. through the channel until the foam becomes soft.

13 Claims, 2 Drawing Sheets

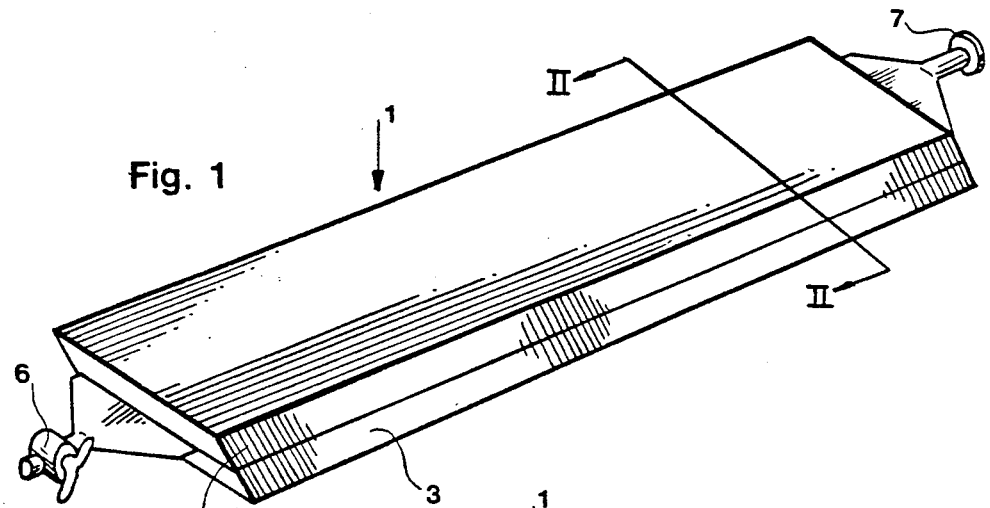
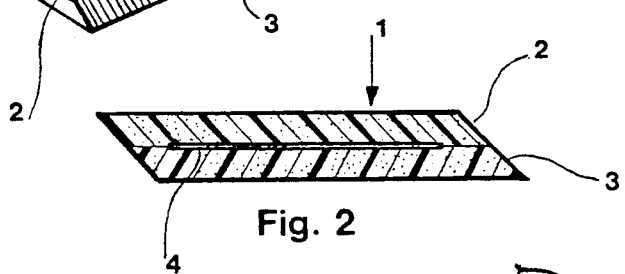
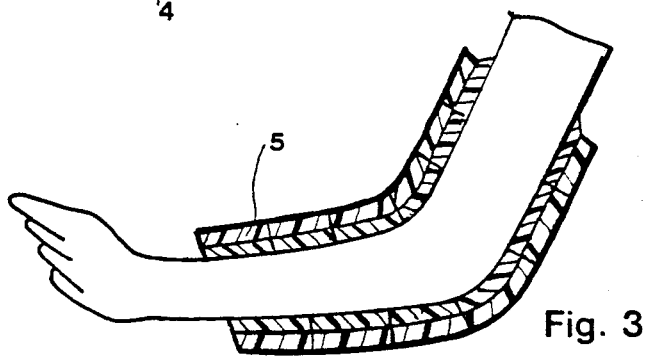
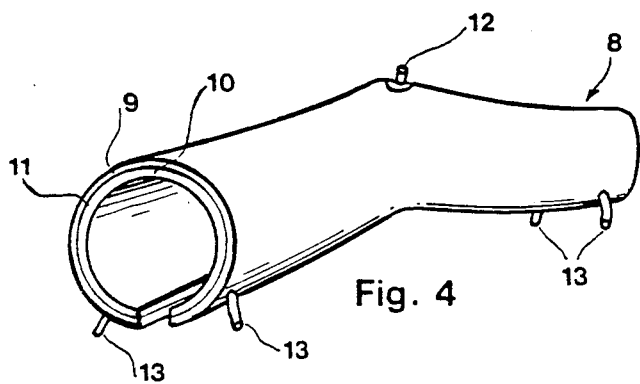

THERMOFORMABLE ORTHOPEDIC BANDAGE AND USE THEREOF

This is a division of application Ser. No. 734,314 filed May 14, 1985, now U.S. Pat. No. 4,685,453.

BACKGROUND OF THE INVENTION

The present invention relates to thermoformable elements, of the kind comprising two adjacent layers of polymers at least one of which comprises an elastically compressible foam, at least one of the layers being made of a thermoplastic polymer, and to a use of such element.

The use of thermoplastic polymer foams, in particular polyethylene, has already been proposed in the medical field, particularly as an orthopaedic support for immobilising fractured limbs. To this end, the foam is heat-moulded around the part of the body to be bandaged. Foams of this type have also been used to fit a prosthesis to an amputated limb. To this end, the foam is heated to its thermoforming temperature which is approximately between 130° and 140° C. and is applied to the part of the body to which it is to be fitted, by modelling it until it takes the form of that part of the body.

Other applications for the foam have been proposed, in particular in European Patent No. A 2 0 004 829, in which the foam is associated with an electric heating body in order to enable moulding of the foam, a rough cast of which has been made previously for fitting closely a non-extensible, in particular rigid, casting, to a part of the human body.

Although the association of an electric heating body is possible in the case of an industrial item which, by definition, is mass produced with the same dimensions, this solution is difficult to adapt for medical use, in particular orthopaedic use, in that each bandage not only has to correspond to the shape and size of the patient, but also to the fracture or fractures, as well as to the location thereof. In view of these constraints, it would be inconceivable, in practice, to make electric heating bodies dimensioned according to the size of each bandage, since this solution would lead to a multiplicity of heating bodies, and to form them in such a way as to produce homogeneous heating across the entire surface of the bandage, which is extremely difficult to carry out and has to be studied from case to case. This condition is of great importance for thermoforming since foams of this type have very poor thermal conductivity, so that the density of current per section of the heating body has to be as constant as possible for each portion of the foam surface to be thermoformed.

For this reason it has been proposed to make orthopaedic supports using thermoformable materials without incorporating heating means therein. The orthopaedist cuts pieces of thermoformable materials to the required dimensions or buys elements which are sold ready cut, heats them in an oven or in a hot water bath according to the thermoforming temperature of the material used and then forms it on the patient. An orthopaedic bandage of this type is described in French Patent No. 1 570 760. In this case, a sheet of a thermoplastic material which is rigid at room temperature is inserted between two sheets of a foam made of thermoplastic material, in order to provide support for the limb to be immobilised.

In French Patent No. 2 120 515 a splint has also been proposed which comprises a rigid shell the inner face of which is lined with a type of impervious cavity formed by a flexible casing. A fluid or material which can be hardened can be injected into the cavity in order to immobilise the limb inside the rigid shell. A solution of this type is difficult to produce on an industrial scale in that different sizes of shell have to be produced, the shell having unchangeable dimensions.

Another factor which should be considered in thermoforming is the compatibility of the thermoforming temperature with what the skin can withstand. In the case of flexible foams, such as those used for example in French Patent No. 1 570 760, their low density makes it possible to withstand a relatively high thermoforming temperature. On the other hand, in the case of denser materials, for example materials which are rigid at room temperature, a temperature of 50° to 60° C. cannot be exceeded if the technique of heating in an oven is used and if the materials are to be applied around the limb to be immobilised whilst they are still soft. This has made necessary the development of special materials for this application which are very expensive, so that their use is restricted as a result.

The object of the present invention is to provide a thermoformable element which ensures even heating of the entire surface of the foam to be thermoformed, whatever the shape or size of the surface.

SUMMARY OF THE INVENTION

The present invention resides in a thermoformable element comprising two adjacent layers of polymers one of which at least one comprises elastically compressible foam, and at least one layer is made of a thermoplastic polymer, characterised in that the edges of the layers define between them an enclosed space connected to the outside by at least two openings one of which comprises an inlet for a fluid for heating the said thermoplastic polymer to its thermoforming temperature and the other of which comprises an outlet for this fluid.

The invention has many advantages. The heating fluid can circulate across the entire surface to be heated and thus heat it evenly. The element can be made for example in the form of a very long strip and cut to the required length according to the bandage to be made. Heating the bandage internally means that because of the large drop in temperature through the layers of foam, the element can be thermoformed without its outer surface that makes contact with the skin, reach a temperature much greater than that of the human body. Consequently, it is possible without further steps to use inexpensive thermoplastic polymers which are commercially readily available. The enclosed space in which the heating fluid circulates can also be used to circulate a cooling fluid, in particular to accelerate foam hardening after the thermoforming operation.

BRIEF DESCRIPTION OF THE DRAWINGS.

Other features and advantages of the invention will become apparent from the following description and the attached drawings which illustrate diagrammatically and by way of example only thermoformable elements embodying the present invention. In the drawings:

FIG. 1 is plan view of a first embodiment.
FIG. 2 is a section along II-II of FIG. 1.

FIG. 3 is a section of a bandage made using this embodiment.

FIG. 4 is a perspective view of a second embodiment.

Figure 5:
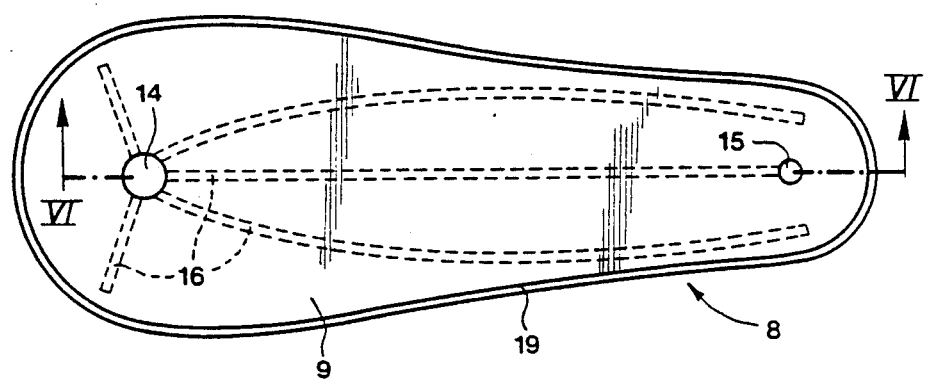
FIG. 5 is a plan view of a third embodiment.

DESCRIPTION OF PREFERRED EMBODIMENTS.

FIGS. 1 and 2 illustrate a strip 1 comprising two layers of foam 2 and 3 made of a thermoplastic polymer, in particular low density polyethylene. The layers are welded to one another along their two longitudinal edges in such a way as to form between them a space in the form of a channel 4. This welding operation can be performed by ultrasonic thermal welding in particular. The two longitudinal edges of the layers of foam 2 and 3 can also be stuck together using, for example, a contact type adhesive. FIG. 2 shows that the cross section of the strip 1 preferably has the shape of a rectangular parallelogram, in order to facilitate the join between the two adjacent longitudinal edges when the strip 1 is wound in the manner of a spiral around a generally cylindrical part of the human body. One of the outer faces of the strip 1 is preferably coated with a self-adhesive substance.

The channel 4, when not in use, is in the form of a single slot, the two walls of which can be moved apart from one another when a fluid under pressure is passed between the two layers of foam, as will be explained later. The strip 1 can be produced in a continuous manner and packaged in the form of rolls each formed from a strip several meters in length. The strip can then be cut to the required length according to the bandage to be made.

In order to thermoform the bandage around the fractured limb, a hot fluid is passed under pressure through the channel 4. The walls of the slot move apart to allow the passage of the fluid. The fluid can be, for example, hot air or water vapour the temperature of which is approximately 130° to 140° C., which is the thermoforming temperature of the foam forming the layers 2 and 3. The fluid emerges at the other end of the channel 4. The foam softens gradually. When it is sufficiently soft, the temperature on the outer surface of the strip is approximately 40° C. The passage of the fluid through the channel 4 is then stopped and the bandage is formed by winding the strip 1 around the fractured limb, tightening it sufficiently so that the strip adopts the shape of that part of the body. The bandage is then left to cool and can then be covered with plaster (FIG. 3) or a shell 5 made of thermoplastic material, which is also fitted by thermoforming around the bandage. The shells are usually made from polypropylene strips.

The thermoforming temperature of polypropylene is approximately 200° to 240° C., but the foam bandage acts as an insulator which prevents the patient from being burned, so that the shell can be formed directly in situ. However, in order to prevent the polyethylene foam from melting during moulding of the polypropylene shell, a cooling fluid can advantageously be passed through the channel 4. The fluid is used to protect both the foam and the patient. The channel 4 thus also enables the moulding of the propylene shell 5 on the patient, which is a great simplification. Shells of this type could not hitherto be made of polypropylene in situ because of its high thermoforming temperature; instead, it was necessary to use acrylic type materials such as that which is known under the registered trademark orthoplast, the price of which is much greater than that of polypropylene.

As illustrated in FIG. 1, after cutting the strip 1 to the required length, its two ends can be provided with a non-return valve 6 at the inlet and a plug 7 at the outlet. During the heating operation to thermoform the strip 1, the plug 7 is open. The pressure loss which it causes ensures even distribution of the heating fluid in channel 4.

A certain amount of time after the formation of the bandage formed by thermoforming the strip 1 and the placing of or shell 5 applied around the bandage, the muscles of the immobilised part of the body atrophy, so that clearance is created between that part of the body and the bandage. The clearance can be taken up by injecting a fluid under pressure into the channel 4 of the strip 1, after closing the plug 7. The walls of the slot comprising the channel 4 move apart and the clearance is thus eliminated. The pressure thus produced around the bandaged part of the body can moreover be adjusted by the patient or by the doctor. To ensure proper imperviousness of the space between the foam layers, an impervious film such as PVC film can be applied to the internal faces of the foam layers 2 and 3. A proper air chamber could also be disposed in the channel 4 to which the valve 6 and the plug 7 would be secured, e.g. by adhesion or by heat welding.

The invention is not limited to the embodiment in which the thermoformable element is in the form of a bandage. As shown in FIG. 4, the bandage can also be in the form of a rough cast of a part of the body, for example the leg or knee. The basic idea, however, remains identical to that of the strip. The bandage 8 in FIG. 4 comprises two layers of foam 9 and 10 welded or stuck together on their respective edges, and forming an enclosed space 11. In this embodiment. the bandage 8 is provided with a non-return valve 12 and four plugs 13. The principle is identical to that of the strip 1. A hot fluid between 130° and 140° C. is passed through the valve 12 and emerges via the openings of the plugs 13. The rough cast heated in this way to the thermoforming temperature is then applied around the leg of the patient; care is taken, in particular, to mould closely the pressure points below the knee, above the fracture to allow a support (not shown) to be associated with the bandage. As in the case of the previous embodiment, a rigid shell made of plaster or polypropylene in particular can be formed around the bandage 8. In the case of forming the shell of polypropylene in situ, a cooling fluid can also be passed in the space arranged between the two layers of foam 9 and 10, as described above.

Polyethylene foams with closed pores have the property of returning to their original shape when they are reheated to their thermoforming temperature, so that the bandage can be thermoformed several times in succession if it proves to be necessary to change the immobilisation position of the limbs.

The above description illustrates the extreme flexibility in use of the thermoformable element which is the subject of the invention both in its strip form and in the form of a preformed sleeve in FIG. 4. In the latter case, it can be seen that different sizes of sleeve can be made industrially to allow fitting for the entire population. The thermoformable element also simplifies the work of the orthopaedist in that it is no longer necessary to make a preform of the leg or arm in order to make a moulding structure, since all the moulds, that of the bandage and the shell surrounding the bandage, can be made directly in situ. The means for heating the thermoformable element also eliminates any risk of burning. The space between the layers of foam can be used not only for heating, but also for cooling and by closing it at its inlet or outlet(s) can be used to hold a fluid under pressure to fill up the clearances due to atrophy of the muscles. To this end, the fluid used can also be a gel.

In the case where the thermoformable element is in the form of a flat or preformed rough cast of the type of that in FIG. 4, the rigid shell preferably comprises directly the outer layer 9 of the bandage 8. Advantageously, the outer layer 9 which is rigid at room temperature can be made from a sheet of ethylene-vinyl acetate co-polymer 3.2mm thick, such as that sold under the trade name "Worblex Electra ® 7013" by Gurit-Worbla AG in Ittigen in the canton of Bern (Switzerland). This product has a density of $1.16 kg/dm^3$ at 23° C. and a VICAT softening point at 73° C. The foam which is associated with it as an internal layer 10 comprises a sheet of polyethylene reticulated by irradiation of 4mm thickness with a density of $67 kg/m^3$ and the thermoforming temperature of which is approximately 120° C. The foam is sold in particular under the trademark Alveolit ® 1500 by Alveo AG in Lucerne (Switzerland).

In a case of this type where the two layers 9 and 10 are made of materials which cannot be heat welded, the edges of the adjacent layers are secured to one another by sticking using a contact adhesive, by stitching or by an adhesive strip 19 (FIG. 6) in particular. If the two layers are of the same material or of two materials which can be welded together at their softening temperature, the edges of the layers can be welded as already stated. However, with heat weldable materials of this type it is then necessary, if the element is to be thermoformed several times, to spread talc or magnesia inside the enclosed space defined between the two layers in order to prevent their sticking when the thermoforming takes place.

Figure 6:
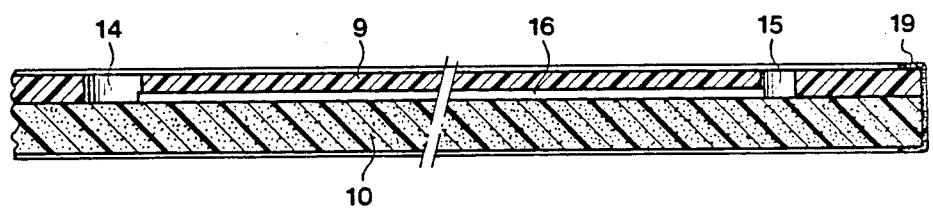
FIG. 6 is a section along line VI-VI of FIG. 5.
Figure 7:
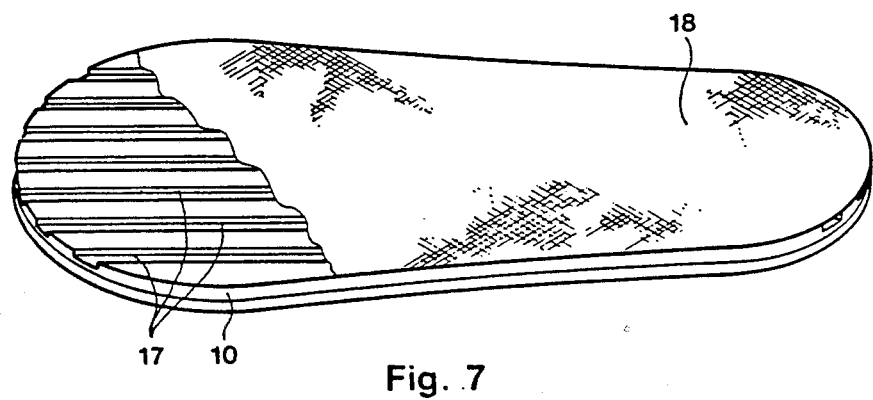
FIG. 7 is a perspective view of a fourth embodiment.

In the case of relatively extensive surfaces, it is necessary to take steps to provide even irrigation of the entire space by the heating fluid. As illustrated in FIGS. 5 to 7, the steps consist firstly in arranging an inlet opening 14 near to the edge of the enclosed space defined between the adjacent layers 9 and 10, the cross section of which is substantially greater than that of the outlet opening(s) 15, in such a way as to cause pressure loss. The second step consists in arranging irrigation channels 16 in the thickness of one of the layers connecting the inlet opening 14 to the outlet opening(s) 15. The channels 16 have, in this example, a cross section of approximately $1 mm^2$. The object of these is to distribute the heating fluid under pressure across the entire surface of the enclosed space. Since the pressure loss occurs at the outlet of the fluid under pressure, the adjacent layers 9 and 10, at least one of which is elastically deformable, are forced apart from one another so that the fluid is distributed between the channels and thus irrigates the entire space, producing even heating of the adjacent layers 9 and 10 at their thermoforming temperature. It is not necessary for each irrigation channel 16 to terminate in an outlet opening, it is also useful to arrange intermediate irrigation channels 16a which do not terminate in any outlet. The distance between the irrigation channels 16 or 16a is approximately 10cm.

In the case where a large surface is to be formed, for example in the case of a corset, it can be advantageous to provide ventilation for the foam surface in contact with the skin either directly or preferably by interposing a knitted fabric 18. As shown in FIG. 7, ventilation occurs by means of channels 17 arranged in the thickness of the inner layer 10 and arranged so as to occupy a substantially vertical position so that the air circulates by the chimney effect. The presence of a knitted fabric 18 between the foam 10 and the skin means that the suction effect on the skin, similar to that of a suction cup, can be avoided or reduced. This enables, in particular, channels 17 of sufficient cross section to be arranged to provide good air circulation. $3 \times 3mm$ channels achieve good results. If there is no provision for the presence of a knitted fabric, the cross section of the channels can be reduced to approximately $1 \times 1mm$.

According to a modification which is not shown, instead of using two layers which are welded, stuck, stitched together or secured by an adhesive strip 19 (FIG. 6), the layers could be formed by compression moulding a tube of extruded foam. In a case of this type, the two layers are of necessity made of a foam of the same material, so that the inside has to be coated with talc to prevent sticking during thermoforming.

Another modification is also be possible in which the outer layer comprises neither flexible foam nor a material which is rigid at room temperature, but an elastic knitted fabric impregnated with PVC to make it impervious, the inner layer being made of a foam of a thermoformable material secured to the knitted fabric according to one of the above-mentioned securing methods in order to arrange an enclosed space between their edges. A knitted fabric of this type can be used for example to closely bind an ankle by means of lacing, the thermoforming of the foam enabling the pressure of the elastic knitted fabric to be distributed evenly.

As has been stated above, the means for heating the thermoformable element according to the invention comprises a hot fluid passed into the enclosed space arranged between the two layers of the element. According to one modification, it is also possible to heat flat products made using, for example, a layer of rigid polyethylene 9 and a layer of polyethylene foam 10 (FIG. 5) with closed pores by introducing cold water into the enclosed space arranged between the two layers. The water can be introduced by connecting the outlet opening 14 (FIGS. 5 and 6) to a mains water tap or likewise by wetting the element in a basin of water. In the latter case, the water distribution can be improved by the presence of a hydrophilic layer, such as cotton wool, between the layers of polyethylene. The element is then placed in a microwave oven where the water is heated, is transformed into steam and emerges from the enclosed space via openings 14 and 15, heating the enclosed space and imparting the heat to the layers 9 and 10 from inside the element, in exactly the same way as steam or hot air under pressure.

It may also be pointed out that, in the case of large surfaces, points or lines can be provided for securing the two layers inside the enclosed space in order to prevent one layer from sliding relative to the other.

Although the invention has been described in particular in connection with its use as an orthopaedic bandage, other applications of the invention are also considered as being covered by the protective scope. Thus an element of this type can be used as a thermoformable sealing joint, a thermoformable mattress for burns, car seats, etc.

We claim:

1. A method of forming an orthopaedic bandage, comprising the steps of providing a thermoformable element comprising two adjacent layers of polymers of which at least one comprises elastically compressible foam, and at least one layer is made of a thermoplastic polymer, which two layers are united at the edges of the layers so as to define between the layers an enclosed space, and in which at least two openings are provided for connecting the said space to the exterior of the elements, one of which openings comprises an inlet for a fluid for heating the said thermoplastic polymer to its thermoforming temperature and the other of which openings comprises an outlet for this fluid, filling the said space with a heating fluid, heating the element by said fluid to soften at least one layer of said element, applying said softened element to a patient and causing it to adopt a desired shape, and cooling the said element in said desired shape.

2. A method as in claim 1 in which the cooling of the element comprises passing a cooling fluid through said space.

3. The method of using an orthopedic bandage wherein the bandage comprises two adjacent layers of polymers at least one of which comprises elastically compressible foam, and at least one of which is made of a thermoplastic polymer which is rigid at room temperature, which two layers are united at the edges of the layers so as to define between the layers an enclosed space, and in which at least two openings are provided for connecting the said space to the exterior of the elements, one of which openings comprises an inlet for a fluid for heating the said thermoplastic polymer to its thermoforming temperature and the other of which openings comprises an outlet for this fluid, and wherein said space is filled with a heating fluid so as to heat and soften said thermoplastic polymer, the softened bandage is applied to a patient so that the bandage adopts a desired shape, and the bandage is cooled in said shape.

4. An orthopedic bandage as in claim 3 wherein said bandage has a foam face for one of direct and indirect application on the skin which face has ventilation channels positioned to be substantially vertical.

5. A method of use according to claim 3, characterised in that both of said layers are made of a thermoplastic polymer foam.

6. A method of use according to claim 3, further including a non-return valve and a plug respectively controlling the said inlet and outlet openings.

7. A method of use according to claim 3, characterised in that the said edges are secured to one another by heat welding.

8. A method of use according to claim 3, further including an impervious film associated with the adjacent faces of the said layers.

9. A method of use according to claim 3, characterised in that it is made in the form of a strip formed from two longitudinally welded layers.

10. A method of use according to claim 3, characterised in that one of the outer faces of the bandage is self-adhesive.

11. A method of use according to claim 3, characterised in that one of said layers is made of an elastically extensible material.

12. A method of use according to claim 3, characterised in that the cross section of the inlet opening is greater than that of the outlet opening.

13. A method of use according to claim 3, characterised in that one of the faces forming the said enclosed space is provided with irrigation channels beginning at the inlet opening and distributed evenly across the surface on which the heating fluid is to be distributed.

* * * * *